US007879999B2

(12) United States Patent
Delalu et al.

(10) Patent No.: US 7,879,999 B2
(45) Date of Patent: Feb. 1, 2011

(54) METHOD FOR THE SYNTHESIS OF EXOCYCLIC DERIVATIVES OF CYCLOALKYL-HYDRAZINES AND EXOCYCLIC DERIVATIVES OF HETEROCYCLOALKYL-HYDRAZINES

(75) Inventors: Henri Delalu, Lyons (FR); Cécile Colas-Duriche, Talence (FR); Jacques Berthet, Lyons (FR); Philippe Leurent, Toulouse (FR)

(73) Assignees: Isochem, Paris (FR); Centre National de la Recherche Scientifique (CNRS), Paris (FR); Universite Claude Bernard Lyon, 1, Villeurbanne (FR)

( * ) Notice: Subject to any disclaimer, the term of this patent is extended or adjusted under 35 U.S.C. 154(b) by 923 days.

(21) Appl. No.: 10/583,284

(22) PCT Filed: Dec. 17, 2004

(86) PCT No.: PCT/FR2004/003288

§ 371 (c)(1),
(2), (4) Date: May 23, 2007

(87) PCT Pub. No.: WO2005/058852

PCT Pub. Date: Jun. 30, 2005

(65) Prior Publication Data

US 2007/0249829 A1    Oct. 25, 2007

(30) Foreign Application Priority Data

Dec. 17, 2003   (FR) .................................. 03 14795

(51) Int. Cl.
*C07D 211/56*  (2006.01)
*C07D 223/12*  (2006.01)
*C07D 295/22*  (2006.01)
*C07D 295/30*  (2006.01)

(52) U.S. Cl. ...................... 540/605; 544/164; 544/382; 546/184; 546/244; 548/557

(58) Field of Classification Search ...................... None
See application file for complete search history.

(56) References Cited

U.S. PATENT DOCUMENTS 2,806,851 A * 9/1957 Sisler et al. ................. 546/244

| 2,808,439 | A | * | 10/1957 | Barrett et al. | 564/118 |
|---|---|---|---|---|---|
| 2,901,511 | A | * | 8/1959 | Hurley | 564/466 |
| 4,066,698 | A | * | 1/1978 | Clasen | 564/314 |
| 5,101,040 | A | | 3/1992 | Cohen | |
| 5,514,806 | A | * | 5/1996 | Rrbczynski et al. | 546/244 |
| 7,045,659 | B2 | * | 5/2006 | Delalu et al. | 564/118 |
| 7,390,929 | B2 | * | 6/2008 | Delalu et al. | 564/466 |
| 2008/0306274 | A1 | * | 12/2008 | Grossi et al. | 546/244 |

FOREIGN PATENT DOCUMENTS

| EP | 0 277 267 A1 | 8/1988 |
|---|---|---|
| FR | 2 651 776 A1 | 3/1991 |
| GB | 1095040 | 12/1967 |

OTHER PUBLICATIONS

Jain, S. R. et al., "Synthesis of Methylhydrazine in Nonaqueous Solvents", Inorganic Chemistry, 19, 2192-2195, 1980.*
Jain, S. R. et al., "Syntheses of Some N-substituted Hydrazines by the Anhydrous Chloramine Process", Proc. Indian Acad. Sci. (Chem. Sci.), 95(4), 381-389, 1985.*
Diamond et al., "Preparation of N-Substituted Hydrazines from Amines and Chloramine," *J. Am. Chem. Soc.*, 1955, vol. 77, p. 3131.
International Search Report dated Apr. 26, 2005 for PCT/FR2004/003288.
International Search Report dated Apr. 29, 2005 for PCT/FR2004/003286.

* cited by examiner

*Primary Examiner*—Fiona T Powers
(74) *Attorney, Agent, or Firm*—Alston & Bird LLP

(57) ABSTRACT

The invention relates to a method for the synthesis of exocyclic derivatives of cycloalkyl-hydrazines and exocyclic derivatives of heterocycloalkyl-hydrazines The invention is characterised in that the method comprises a step consisting in demixing a solution containing said synthesised derivative, by reacting a heterocyclic amine with monochloramine, in an organic phase and an aqueous phase with the addition of anhydrous sodium hydroxide. According to the invention, the starting amine which has not reacted is collected and reused directly without any additional treatment. The inventive method can also be used to obtain the corresponding exocyclic heterocycloalkyl-hydrazine or cycloalkyl-hydrazinederivative derivative at a low cost compared to that of other known methods.

22 Claims, 2 Drawing Sheets

Figure 1:
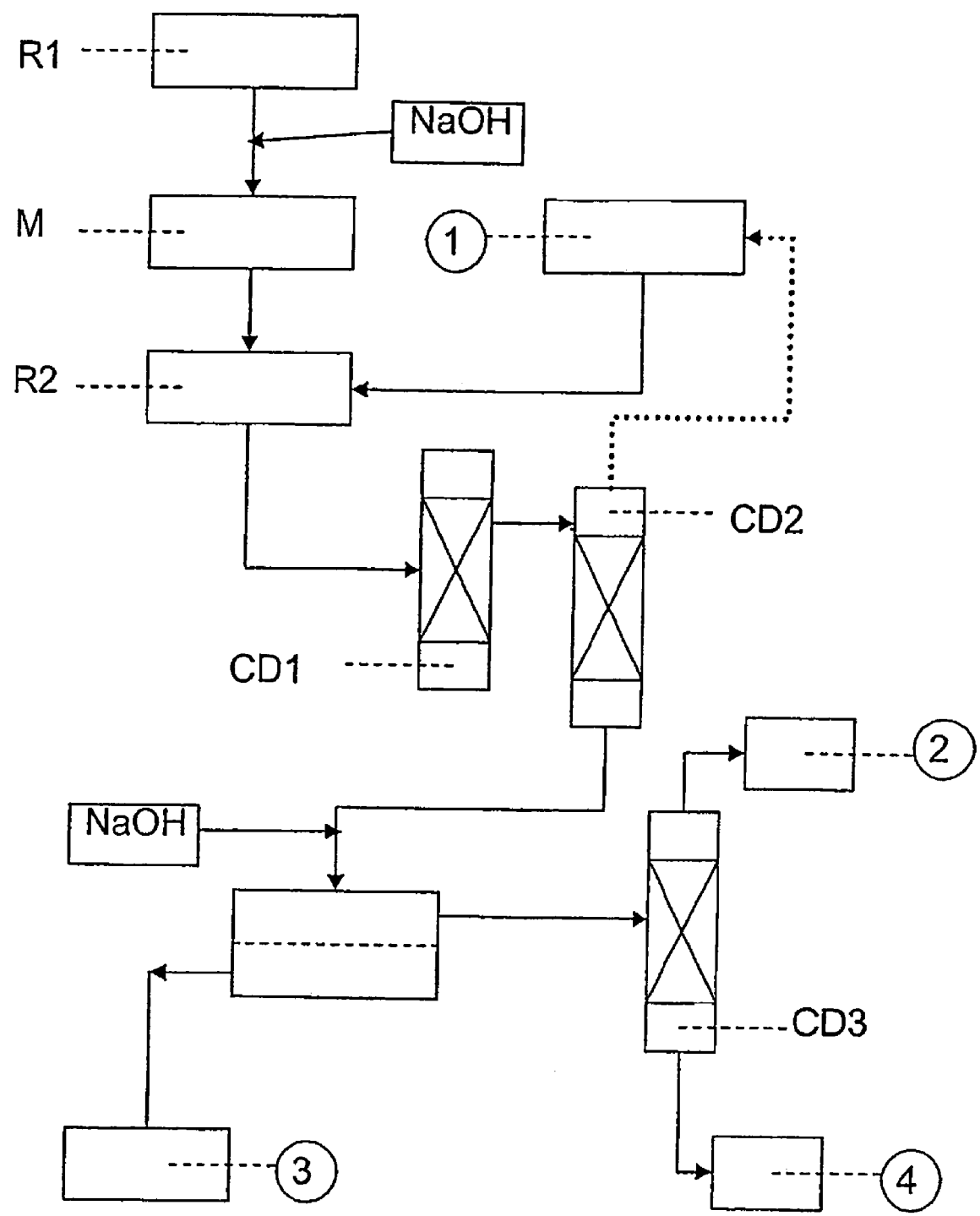

METHOD FOR THE SYNTHESIS OF EXOCYCLIC DERIVATIVES OF CYCLOALKYL-HYDRAZINES AND EXOCYCLIC DERIVATIVES OF HETEROCYCLOALKYL-HYDRAZINES

The present invention concerns a novel method for synthesizing derivatives of exocyclic cycloalkyl-hydrazines and derivatives of exocyclic heterocycloalkyl-hydrazines.

The derivatives of exocyclic cycloalkyl-hydrazines and heterocycloalkyl-hydrazines, in particular N-aminopiperidine, are very frequently used as intermediates in the manufacture of medicinal products.

At the present time, the methods for synthesizing derivatives of exocyclic cycloalkyl-hydrazines and heterocycloalkyl-hydrazines described in the scientific literature have recourse to urea and nitrosamines. For the synthesis of N-aminopiperidine for example, one first synthesis method performed in three steps consists of preparing 1-piperidyl urea followed by oxidation with sodium hypochlorite. The 1-piperidyl-3-chloro-urea formed is then converted into N-aminopiperidine under the action of a concentrated sodium hydroxide solution [R. Ohme, H. Preuschhof, J. Prakt. Chem. 312, 349 (1970)]. A second method consists of nitrosation of piperidine followed by chemical (LiAlH$_4$) or catalytic (Zn/AcOH) hydrogenation of the nitrosated derivative (1-nitrosopiperidine) [Allen & Hamburys Ltd. (1965), 74, 3693-4]. In all cases the nitrosated compound must be purified by distillation. This method leads to fairly good yields (75%). However, the product derived from the first step must be handled with great precaution on account of its toxicity (highly carcinogenic compound) which at industrial level raises operating problems. In addition, the use of LiAlH$_4$ requires the absence of traces of water, sealed reactors and anhydrous solvents (diethyl ether) which have the effect of increasing the risks of combustion of the reaction mixture.

Also, it is acknowledged that for the preparation of the different hydrazines, recourse is often made to the so-called "Raschig" reaction which consists of synthesizing monochloramine by reaction of ammonia over a sodium hypochlorite solution and then causing the formed monochloramine to react on an amine to obtain the corresponding hydrazine. This process requires two separate steps, the first being a cold step for synthesis of the monochloramine and the second being a hot step during which the actual synthesis of the hydrazine is conducted. In addition, the monochloramine must be in the presence of sufficient excess amine in the intermediate solutions so as to avoid secondary degradation reactions, and subsequently the method requires very high quantities of solutions to be treated.

However this method cannot be applied to the preparation of all exocyclic alkyl- and heteroalkyl hydrazines, and especially not to the preparation of organic hydrazines that exhibit thermal decomposition at high boiling temperature. In particular the treatment of the synthesis solutions requires the extraction of water then of the amine, which entails costly operations.

Patent EP 0 277 267 describes a continuous synthesis method for N-amino aza-3 bicyclo [3,3,0] octane, characterized in that a solution of ammonium hydroxide and ammonium chloride is caused to react with an aqueous solution of sodium hypochlorite at a temperature of between −15° C. and −7° C. in an alkaline medium, and subsequently the formed monochloramine is caused to react with aza-3 bicyclo [3,3,0] octane, in a two-phase medium in a suitable reactor provided with a coaxial paddle agitator at a temperature of between 30° C. and 90° C. and in an alkaline medium, the ammonia is separated from the reaction medium and then the aza-3 bicyclo [3,3,0] octane which has not reacted by distillation for its recycling, then a concentrated solution of N-amino aza-3 bicyclo [3,3,0]octane is isolated by demixing through the addition of sodium hydroxide to the reaction medium, and the hydrazine thus obtained is purified, if required, by distillation.

After formation of N-amino aza-3 bicyclo [3,3,0] octane and cooling, the reaction solution is degassed to remove the ammonia, and the amino-3 bicyclo [3,3,0] octane which has not reacted is separated from the reaction medium by ordinary distillation under atmospheric pressure and at a temperature of around 90 to 100° C. Under these conditions, the amine is obtained in the form of an aqueous solution with a 30% concentration of aza-3 bicylco [3,3,0] octane. This solution is recycled.

The inventors have now discovered a novel method for synthesizing derivatives of exocylic cycloalkyl-hydrazines and derivatives of exocyclic heterocycloalkyl-hydrazines, in particular of N-aminopiperidine. This method, implemented continuously, is partly based on transposition of the Raschig process and it consists of preparing monochloramine by action of sodium hypqchlorite on ammonia at low temperature, then of causing the monochloramine produced to act on a heterocylic amine in a homogeneous medium or, according to temperature, in a heterogeneous medium, and then of extracting the hydrazine formed. The starting amine is recycled and optionally re-injected immediately onto the monochloramine with no additional treatment.

Under the present invention, for simplification purposes, the derivative(s) of exocyclic cycloalkyl-hydrazines and the derivative(s) of exocyclic-heterocycloalkyl-hydrazines can be denoted by the term "hydrazine(s)".

In the meaning of the present invention, the expression "derivative of exocyclic cycloalkyl-hydrazine or heterocycloalkyl-hydrazine" is to be construed as "derivative of exocyclic cycloalkyl-hydrazine or derivative of exocyclic heterocycloalkyl-hydrazine".

Similarly the heterocyclic amine(s) may be denoted "amines".

The present invention therefore concerns a method for synthesizing derivatives of exocyclic cycloalkyl-hydrazines and derivatives of exocycyclic heterocycloalkyl-hydrazines, characterized in that it comprises the following successive steps:

a) synthesizing the derivative of exocyclic cycloalkyl-hydrazine or heterocycloalkyl-hydrazine in a suitable reactor by causing a monochloramine to react in an alkaline medium with a heterocyclic amine at a temperature of between 30 and 60° C.; then b) demixing the solution obtained after step a) into an organic phase and an aqueous phase through the addition of anhydrous sodium hydroxide under cooling so that the temperature does not exceed the boiling point of the compounds; and c) optionally, by distillation of the organic phase obtained, isolating the derivative of exocyclic cycloalkyl-hydrazine or heterocycloalkyl-hydrazine.

The derivative of exocyclic cycloalkyl-hydrazine or heterocycloalkyl-hydrazine advantageously has the formula (I):

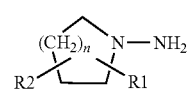

in which one of the carbon atoms of the cycle is optionally replaced by a heteroatom chosen from among a nitrogen or oxygen atom, R1 and R2 identical or different represent a hydrogen atom or a $C_1$-$C_6$ alkyl radical, or R1 and R2 together form a $C_3$-$C_8$ cycloalkyl and n equals 1 to 3.

The derivative of exocyclic cycloalkyl-hydrazine or heterocycloalkyl-hydrazine is further advantageously chosen from the group consisting of N-aminopiperidine, N-aminomorpholine, N-amino-2,6-dimethyl-piperidine, N-aminopyrrolidine, N-aminoazepine, N-amino-4-methyl-piperazine.

The reactor of step a) is advantageously placed in an inert atmosphere, under a stream of argon or nitrogen in particular. Said suitable reactor in step a) is advantageously an agitated tubular reactor. With a tubular reactor it is possible to avoid contact between the nascent hydrazine and the monochloramine thereby avoiding a redox reaction between these two reagents. The reaction front moves along the tube and the hydrazine is no longer in contact with the monochloramine injected into the base of the reactor.

According to one advantageous variant of the invention, the concentration of hydroxyl ions in the reaction medium at step a) lies between 0.3 and 0.8 mol.l$^{-1}$.

The ratio between the molar concentrations of the heterocylic amine and the monochloramine must advantageously be 4 or higher and 10 or lower. The reaction time is variable and depends upon the temperature at which the reaction is conducted and on the concentration ratio of the reagents. For example for the synthesis of N-aminopiperidine, and over the range of given concentration ratios, the reaction time is in the order of 20 seconds to 2 minutes at 25° C. and in the order of 4 seconds to 30 seconds at 60° C.

According to one advantageous embodiment of the present invention, the monochloramine is alkalinised prior to step a) in a mixer through the addition of a strong base solution such as sodium hydroxide so that the weight percentage of sodium hydroxide is between 2 and 6%. Said mixer is advantageously maintained at a temperature of between −10 and 5° C.

The reaction of the monochloramine with the heterocyclic amine is therefore advantageously conducted in the presence of an aqueous solution of sodium hydroxide under heat. On completion of the synthesis reaction of the exocyclic cycloalkyl-hydrazine or heterocycloalkyl-hydrazine derivative, i.e. on leaving the reactor of step a), the sodium hydroxide concentration in the reaction medium is around 0.3 mol.L$^{-1}$. The sodium hydroxide concentration must not be too high otherwise the reaction mixture may demix through salting out. In this case a reactor of agitated piston type must be used.

During the hydrazine synthesis reaction, hydrochloric acid is also formed and any local protonation of the amine must be avoided during mixing to avoid the formation of a substituted chloramine. For example for the synthesis of N-aminopiperidine, the piperidine protonated by hydrochloric acid (piperidinium) may react with the monochloramine to form 1-chloropiperidine, which may then react with the hydroxyl ions to form 2,3,4,5-tetrahydropyridine, which may then trimerize. Alkalinisation of the monochloramine i.e. the addition of a strong base such as sodium hydroxide, enables neutralizing of the acid formed. The quantity of strong base added must be sufficient to neutralize all the acid formed. In addition, the rate of hydrazine formation increases with the alkalinity of the medium which is not the case for the rate of degradation reactions such as oxidation of nascent hydrazine by chloramine.

During step b) the quantity of anhydrous sodium hydroxide added is such that the weight percentage of sodium hydroxide lies between 10 and 35%, preferably approximately 30%.

Under these conditions, the medium demixes into two phases of which one concentrates the formed derivative of exocyclic cycloalkyl-hydrazine or heterocycloalkyl-hydrazine in the light phase (organic phase). This treatment with sodium hydroxide, through demixing, enables elimination of the water present in the reaction medium and extraction of the salts and optionally of the ammonia in the lower phase (aqueous phase).

For the synthesis of N-aminopiperidine for example, the temperature of the demixing medium at step b) must not exceed 80° C.

According to a first advantageous embodiment of the invention the heterocyclic amine is added at step a) in the form of an anhydrous heterocyclic amine.

The monochloramine, advantageously alkalinised, and the anhydrous heterocyclic amine are advantageously added simultaneously to the reactor. The rates at which the heterocyclic amine and the monochloramine are added are such that the ratio between the molar concentrations of the anhydrous heterocyclic amine and the monochloramine advantageously lies between 4 and 10, the limits possibly being included. Part of the synthesis reaction of the exocyclic cycloalkyl-hydrazine and heterocycloalkyl-hydrazine derivative may be conducted in a heterogeneous medium.

The addition of anhydrous sodium hydroxide at step b), advantageously such that the weight percentage of sodium hydroxide is between 15 and 35%, makes it possible to demix the medium into two phases of which one, the upper phase or organic phase, concentrates practically all the organics namely the derivative of exocyclic cycloalkyl-hydrazine or heterocycloalkyl-hydrazine and the heterocyclic amine.

The advantage of this treatment is that it is possible in a single step to remove 80 to 90% by weight of the water present in the reaction medium, according to the organic nature (number of carbon atoms) of the amine and hydrazine molecules, and to extract the ammonia with the salts in the lower phase (aqueous phase).

Step c) then advantageously comprises the following successive steps:

i) isolating the heterocyclic amine which has not reacted and a concentrated solution of the derivative of exocyclic cycloalkyl-hydrazine or heteorcycloalkyl-hydrazine by distillation of the organic phase obtained after step b); then ii) optionally rectifying, by distillation and under reduced pressure, said concentrated solution of the derivative of exocyclic cycloalkyl-hydrazine and heterocycloalkyl-hydrazine.

During step i), distillation is advantageously performed in a single distillation column under atmospheric or reduced pressure, in relation to the boiling point of the starting amine. Initially a concentrated solution of heterocyclic amine is collected at the head of the column, or optionally an azeotropic solution of water-heterocyclic amine, until exhaustion of the water, then the anhydrous heterocyclic amine.

The anhydrous heterocyclic amine thus collected can be directly re-injected into the reactor of step a) where the synthesis of hydrazine takes place. The heterocyclic amine obtained in the form of a concentrated solution or azeotropic solution with water can be collected and optionally re-injected after suitable treatment.

Optionally by rectifying under reduced pressure, advantageously at around 115 mm Hg, the product obtained at the foot of the column in step i) it is possible to collect the derivative of exocyclic cycloalkyl-hydrazine or heterocycloalkyl-hydrazine with a titer of 99%, advantageously greater than 99.9%.

Said derivative of exocyclic cycloalkyl-hydrazine or heterocycloalkyl-hydrazine must then be stored in an inert atmosphere such as argon to avoid any oxidation reaction with oxygen.

This variant of the invention is particularly advantageous for the batch preparation of the derivative of exocyclic cycloalkyl-hydrazine or exocyclic heterocycloalkyl-hydrazine.

According to a second advantageous variant of the invention, the heterocyclic amine is added at step a) in the form of a concentrated aqueous solution of heterocyclic amine or an azeotropic solution of water-heterocyclic amine. Step a) is then performed in a homogeneous or heterogeneous medium (when the amine is very heavy).

In relation to the amine under consideration, the concentrated aqueous solution of heterocyclic amine can be in the form of a water-heterocyclic amine azeotrope.

The monochloramine, preferably alkalinised, and the solution of heterocyclic amine are advantageously added simultaneously to the reactor. The rates at which the concentrated aqueous solution of heterocylic amine, or azeotropic water-heterocyclic amine solution, and the monochloramine are added are such that the ratio of the molar concentrations of the heterocyclic amine solution to the monochloramine advantageously lies between 4 and 10, the limits possibly being included.

During step a), the reaction mixture can optionally undergo one or more degassing steps to remove the ammonia contained in said mixture.

In this second variant of the invention, after step a) and prior to step b) the method comprises the following steps:

i') removing the ammonia present in the solution obtained after step a) by stripping; then ii') isolating a solution comprising the formed derivative of exocyclic cycloalkyl-hydrazine or heterocycloalkyl-hydrazine and a concentrated solution of heterocyclic amine which has not reacted, or optionally an azeotropic water-heterocyclic amine solution which has not reacted, by distillation of the solution obtained after step i') under atmospheric or reduced pressure at a temperature of between 50 and 180° C.; and iii') re-injecting into the: reactor of step a) said aqueous concentrated or azeotropic solution of heterocyclic amine obtained after step ii').

In the meaning of the invention, by "stripping" is meant the removal of a very volatile product, in this case ammonia, by mere heating of the mixture.

The reaction solution containing the hydrazine, collected at step ii'), is then treated with the addition of a strong base such as sodium hydroxide (step b). This operation allows separation of the derivative of exocyclic cycloalkyl-hydrazine or heterocycloalkyl-hydrazine in an organic phase with a hydrazine content of between 70 and 90% depending upon the organic nature of the hydrazine molecule. In accordance with specifications for use, the concentrated hydrazine solution obtained may be used directly or distilled under reduced pressure (step c).

The recycling of the amine during distillation step ii') is conducted without hydrazine entrainment and at a temperature below the boiling point of the amine to avoid its thermal decomposition. Since there are no traces of hydrazine in the aqueous solution containing the heterocyclic amine, optionally in azeotrope form, this solution can be injected with no additional treatment directly into the reactor of step a) in which the hydrazine is formed.

This variant of the invention is of particular advantage for continuous preparation of the derivative of exocyclic cycloalkyl-hydrazine or exocyclic heterocycloalkyl-hydrazine.

The method of the present invention therefore not only enables continuous synthesis of the derivative of exocyclic cycloalkyl-hydrazine or heterocycloalkyl-hydrazine without the formation of any toxic intermediate, but also makes it possible to obtain said hydrazine at low cost.

Conventional Raschig synthesis generally requires a large excess of amine, which amounts to a considerable disadvantage when the amines used as raw material for preparing the corresponding hydrazines are very costly. The method of the present invention, via the collection and recycling of a concentrated solution of heterocyclic amine, optionally in the form of an azeotrope, allows the corresponding derivative of exocyclic cycloalkyl-hydrazine or heterocycloalkyl-hydrazine to be obtained at a very low cost compared with other known processes. The isolating of the amine in the form of an aqueous solution, possibly azeotropic solution, at relatively low temperature also provides a further originality and a considerable economic advantage for the method of the invention.

The monochloramine added at step a) is advantageously prepared using a process comprising the following successive steps:

α) preparing an aqueous solution of sodium hypochlorite with between 36 and 100° chlorometric degrees, optionally by dilution of a hypochlorite solution with between 100 and 120° chlorometric degrees; then β) causing a solution of ammonium hydroxide and ammonium chloride to react with the aqueous solution of sodium hypochlorite obtained after step a) in a low alkaline medium at a temperature between −15 and −7° C. to form said monochloramine.

In the meaning of the present invention, by "low alkaline" medium is meant a medium whose pH is approximately 10±1.

The molar ratio of the ammonium hydroxide and ammonium chloride solution/aqueous solution of sodium hypochlorite is advantageously between 2.5 and 3, the limits included.

The ammonium chloride/ammonium hydroxide molar ratio is advantageously between 0.1 and 1.75, limits included, more advantageously approximately 0.65.

If the chlorinated reagent used at step α) is obtained by diluting a high titer hypochlorite solution with 100-120° chlorometric degrees, this dilution has the advantage of reducing the sodium chloride content by 40%. This treatment, beneficial for the environment, allows cooling of the bleach solution with no risk of crystallization down to −15° C.

Example 1, gives a non-restrictive detailed description of the implementation of the method of the invention, a method outlined in the diagram shown FIG. 1.

Figure 2:
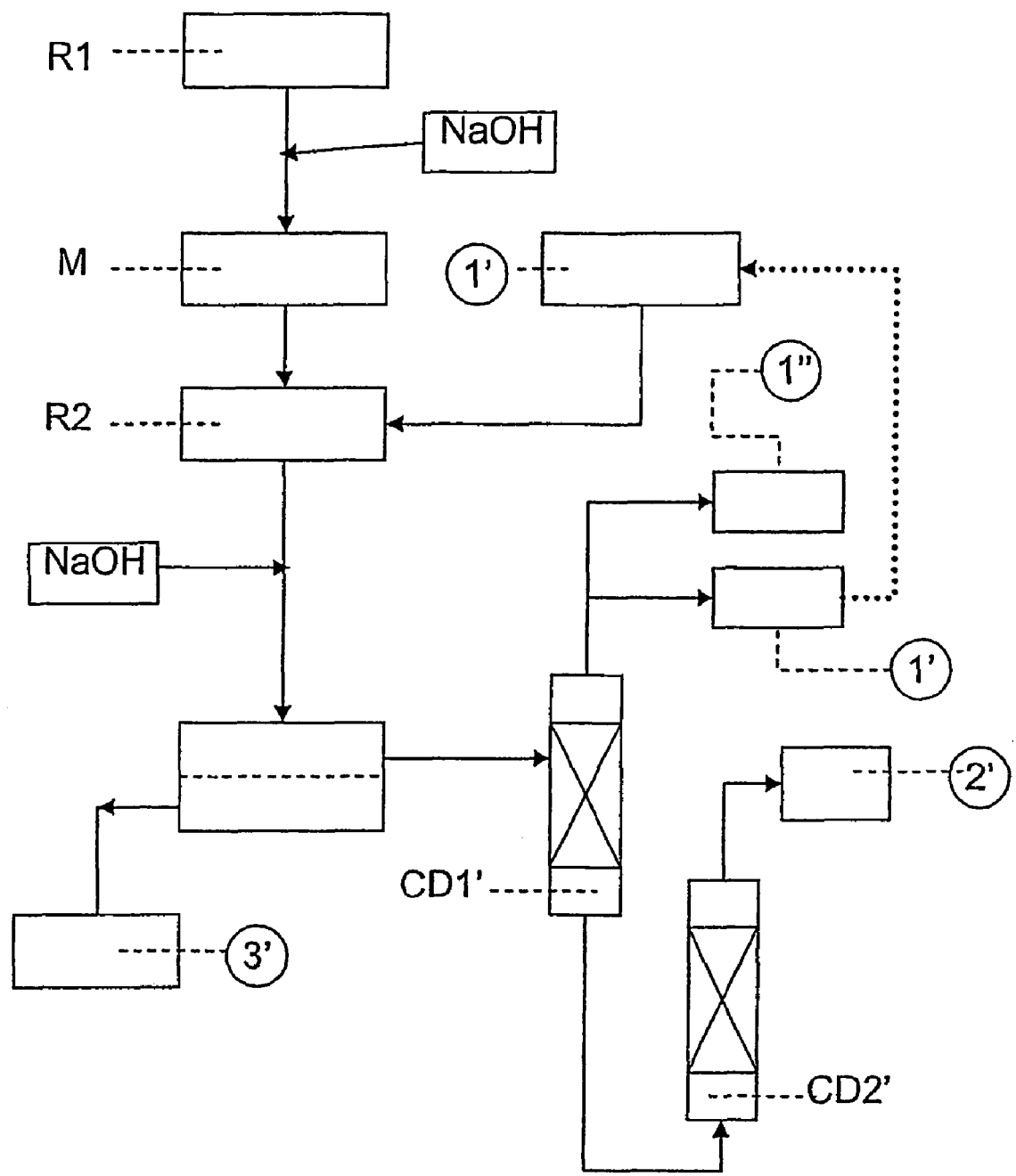

Meaning of the abbreviations used:
R1: reactor 1 M: mixer R2: reactor 2
CD1: distillation column n°1
CD2: distillation column n°2
CD3: distillation column n°3
1: piperidine solution
2: N-amino-piperidine
3: Water+NaCl+NaOH solution
4: residues Example 2 gives a non-restrictive, detailed description of the implementation of the method of the invention, a method outlined in the diagram shown FIG. 2.

Meaning of the abbreviations used:
R1: reactor 1 M: mixer R2: reactor 2

CD1': distillation column n°1'
CD2': distillation column n°2'
1': anhydrous piperidine
1": 66% by weight piperidine solution (water-piperidine azeotrope)
2': N-amino-piperidine
3': Water+$NH_3$+NaCl+NaOH solution

EXAMPLE 1

Continuous Preparation of N-amino piperidine

All the quantities indicated correspond to an operating unit and relate to one liter of injected hypochlorite.

One liter of hypochlorite solution prepared by 50% dilution of a high titer hypochlorite solution (100 to 120° chlorometric degrees, i.e. [NaOCl]=2.14 mol.$L^{-1}$; [NaCl]=0.85 mol.$L^{-1}$) and one liter of solution having an ammonia concentration of 3.60 mol.$L^{-1}$ and ammonium chloride concentration of 2.38 mol.$L^{-1}$ are continuously added to an agitated reactor (R1) at the rate of 5 mL.$min^{-1}$ each (i.e. 6 g/min of hypochlorite solution with 48 chlorometric degrees and 5.05 g/min of the ammonia mixture $NH_3$+$NH_4Cl$).

The temperature inside the reactor is maintained between −8° C. and −11° C. and the pH of the reaction is close to 10. On leaving R1 a monochloramine solution is obtained with a titer of more than 1 mol.$L^{-1}$ which corresponds to a yield close to 100% with respect to the sodium hypochlorite.

On leaving R1 the monochloramine solution obtained above (2 litres) is alkalinised by continuously adding a concentrated solution of sodium hydroxide (0.37 liter at 30% by weight) to the mixer M with double casing maintained at a low temperature between −9° C. and −11° C. Homogenisation is ensured by magnetic driving.

Synthesis of N-amino piperidine is conducted in a monophase medium in an agitated tubular reactor (R2) under a stream of argon or nitrogen.

The $NH_2Cl$/NaOH mixture obtained (2.37 litres) and the piperidine solution (2.36 litres at 66% by weight) are simultaneously and continuously added (under argon or nitrogen) to reactor R2 at a suitable rate so that the molar ratio of piperidine to monochloramine is around 8 and the sodium hydroxide titer in the reaction medium at the end of the reaction is 0.3 mol.$L^{-1}$. The reaction temperature is maintained at approximately 55° C. After 30 seconds' reaction, the reaction mixture then undergoes degassing to remove the ammonia contained in the solution. The reaction solution is firstly rid of ammonia by stripping (distillation column CD1, around 62 g ammonia are collected at the head of the column) then approximately 4.6 kg of the ammonia-free solution are distilled at 92.2° C. under atmospheric pressure (distillation column CD2) to remove the amine which has not reacted, the piperidine. After this distillation step, piperidine is obtained at the head of the column in the form of an aqueous solution whose composition is approximately 66% amine. (around 2 kg). This solution is then recycled and immediately re-injected into R2 with no additional treatment (FIG. 1: dotted arrow).

After separating the piperidine, the reaction solution containing the hydrazine (collected at the foot of column CD2, approx. 2.7 kg) is treated with the addition of solid sodium hydroxide under cooling and a stream of argon to separate the N-aminopiperidine in an organic phase, its titer being almost 70 to 80% hydrazine at 80° C. The weight percentage of the injected anhydrous sodium hydroxide is preferably between 15 and 30% by weight. Therefore the collection is made of said organic phase having a hydrazine content of nearly 92% and an aqueous phase containing the water and salts (NaCl, NaOH). Depending upon the specifications for use, the concentrated hydrazine solution (organic phase) may then be used directly or distilled under reduced pressure (distillation column CD3).

After distillation under reduced pressure, N-aminopiperidine is obtained whose purity is greater than 99.5%.

The hydrazine yield with respect to consumed piperidine is greater than 92%.

EXAMPLE 2

Batch Preparation of N-amino piperidine

All the quantities indicated correspond to an operating unit and relate to one liter of injected hypochlorite.

The method is characterized in that a solution of ammonium hydroxide and ammonium chloride ([$NH_3$]=3.60 mol.$L^{-1}$; [$NH_4Cl$]=2.38 mol.$L^{-1}$; 5 mL/min) is caused to react with an aqueous solution of sodium hypochlorite (rate of 5 mL/min) at a temperature of between −15° C. and −7° C. in an alkaline medium in a continuous agitated reactor R1.

The reaction fluid derived from R1 (2 litres) has a titer of more than 1 mol.$L^{-1}$ monochloramine and is added to a mixer M continuously supplied with a 30% solution of sodium hydroxide (rate 1/75 mL/min). A thermostatic casing maintains a fixed-temperature inside-the mixer of −10° C.

Synthesis of N-aminopiperidine is conducted using an agitated tubular reactor R2 under a stream of argon. The alkalinised monochloramine (2.35 litres) derived from the chamber of the mixer M and the amino reagent are simultaneously added at the base of the reactor by means of metering pumps. 1.69 litres of anhydrous piperidine are added i.e. 1.455 kg since the density is 0.861. The addition rate of the anhydrous piperidine is 8.47 mL/min and part of the reaction is conducted in a heterogeneous medium at 55° C. The final NaOH concentration on leaving R2 is 0.3 mol.$L^{-1}$.

The present variant is characterized in that, to the homogeneous reaction liquid (4.04 litres), a quantity of sodium hydroxide is added of between 13 and 30% under cooling so that the temperature does not exceed 60° C. Under these conditions, two phases are obtained, one light (1.8 kg) contains the entirety of the organics i.e. the N-aminopiperidine and excess piperidine with a titer of around 15 and 20% by weight. With this treatment it is possible to remove between 80 and 85% of the water present in the synthesis solutions.

Obtaining N-aminopiperidine then requires two successive steps:

collecting the piperidine which has not reacted by distilling the organic phase at atmospheric pressure under argon. Initially approximately 1 kg of concentrated amine solution at 66% by weight is obtained (1") at a temperature of 92.2° C. until exhaustion of the water, then approximately 600 g anhydrous piperidine (1') at a temperature of 105° C. (distillation column CD1').

rectifying the solution obtained at the foot of the column, under 115 mm Hg (distillation column CD2').

After distilling under reduced pressure, N-aminopiperidine is obtained that is more than 99.5% pure.

The hydrazine yield with respect to consumed piperidine is greater than 90%.

The invention claimed is:

1. A method for synthesizing derivatives of exocyclic cycloalkyl-hydrazines and heterocycloalkyl-hydrazines of the formula (I):

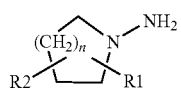

in which, R1 and R2 are identical or different and represent a hydrogen atom or a $C_1$-$C_6$ alkyl radical, or R1 and R2 together form a $C_3$-$C_8$ cycloalkyl radical, and n equals 1 to 3, said method comprising the following successive steps:
(a) synthesizing the derivative of exocyclic cycloalkyl-hydrazine or heterocycloalkyl-hydrazine in a suitable reactor by causing a monochloramine to react with a heterocyclic amine in an alkaline medium at a temperature of between 30 and 60° C.; then
(b) demixing the solution obtained at step (a) into an organic phase and an aqueous phase through the addition of anhydrous sodium hydroxide under cooling so that the temperature does not exceed the boiling point of the compounds.

2. The method of claim 1, comprising, following step (b), a step (c) of isolating the derivative of exocyclic cycloalkyl-hydrazine or heterocycloalkyl-hydrazine by distilling the organic phase obtained.

3. The method of claim 1, wherein the derivative of exocyclic cycloalkyl-hydrazine or heterocycloalkyl-hydrazine is selected from the group consisting of N-aminopiperidine, N-aminomorpholine, N-amino-2,6-dimethyl-piperidine, N-aminopyrrolidine, N-aminoazepine and N-amino-4-methyl-piperazine.

4. The method of claim 3, wherein in formula (I), one of the carbon atoms of the cycle is replaced by a heteroatom chosen from among a nitrogen or oxygen atom.

5. The method of claim 1, wherein at step (a) the heterocyclic amine/monochloramine molar ratio is between 4 and 10.

6. The method of claim 1, wherein the reactor of step (a) is placed in an inert atmosphere.

7. The method of claim 1, wherein prior to step (a), the monochloramine is alkalinized in a mixer through the addition of a solution of sodium hydroxide so that the weight percentage of sodium hydroxide is between 2 and 6%.

8. The method of claim 7, wherein the mixer is maintained at a temperature of between −10 and 5° C.

9. The method of claim 1, wherein the quantity of anhydrous sodium hydroxide added at step (b) is such that the weight percentage of sodium hydroxide is between 10 and 35%.

10. The method of claim 1, wherein the heterocyclic amine is added at step (a) in the form of anhydrous heterocyclic amine.

11. The method of claim 2, wherein the heterocyclic amine is added at step (a) in the form of anhydrous heterocyclic amine.

12. The method of claim 11, wherein step (c) comprises the following step:
(i) isolating the heterocyclic amine which has not reacted and a concentrated solution of the exocyclic cycloalkyl-hydrazine or heterocycloalkyl-hydrazine derivative by distillation of the organic phase obtained after step (b).

13. The method of claim 12, wherein step (c) further comprises, following step (i), a step (ii) of rectifying, by distillation under reduced pressure, said concentrated solution of the derivative of exocyclic cycloalkyl-hydrazine or heterocycloalkyl-hydrazine.

14. The method of claim 1, wherein the heterocyclic amine is added at step (a) in the form of a concentrated aqueous solution of heterocyclic amine.

15. The method of claim 14, wherein the heterocyclic amine is added at step (a) in the form of a water-heterocyclic amine azeotrope.

16. The method of claim 14, wherein after step (a) and prior to step (b), the method comprises the following steps:
(i') removing the ammonia present in the solution obtained after step (a) by stripping; then
(ii') isolating a solution containing the formed derivative of exocyclic cycloalkyl-hydrazine or heterocycloalkyl-hydrazine and an aqueous solution of heterocyclic amine which has not reacted by distilling the solution obtained after step (i') at a temperature of between 50 and 180° C.; and
(iii') reinjecting into the reactor of step (a) said aqueous solution of heterocyclic amine obtained after step (ii').

17. The method of claim 16, wherein said aqueous solution is in the form of an azeotrope.

18. The method of claim 1, wherein the monochloramine is prepared using a method comprising the following successive steps:
α) preparing an aqueous solution of sodium hypochlorite having a chlorometric degree between 36 and 100°; then
β) causing a solution of ammonium hydroxide and ammonium chloride to react with the aqueous solution of sodium hypochlorite obtained after step (a) in a low alkaline medium at a temperature between −15 and −7° C. to form said monochloramine.

19. The method of claim 18, wherein the aqueous solution of sodium hypochlorite is prepared by diluting a hypochlorite solution with between 100 and 120 chlorometric degrees.

20. The method of claim 18, wherein the molar ratio of ammonium hydroxide and ammonium chloride solution/aqueous solution of sodium hypochlorite is between 2.5 and 3.

21. The method of claim 18, wherein the molar ratio of ammonium chloride/ammonium hydroxide is between 0.1 and 1.75.

22. The method of claim 18, wherein the molar ratio of ammonium chloride/ammonium hydroxide is 0.65.

* * * * *

UNITED STATES PATENT AND TRADEMARK OFFICE
CERTIFICATE OF CORRECTION

| | | |
|---|---|---|
| PATENT NO. | : 7,879,999 B2 | Page 1 of 1 |
| APPLICATION NO. | : 10/583284 | |
| DATED | : February 1, 2011 | |
| INVENTOR(S) | : Delalu et al. | |

It is certified that error appears in the above-identified patent and that said Letters Patent is hereby corrected as shown below:

Column 2,

Line 22, "hypqchlorite" should read --hypochlorite--.

Signed and Sealed this
Third Day of April, 2012

David J. Kappos
*Director of the United States Patent and Trademark Office*